United States Patent
Willich et al.

(10) Patent No.: US 10,317,318 B2
(45) Date of Patent: Jun. 11, 2019

(54) EXHAUST-GAS SAMPLING SYSTEM, AND METHOD FOR OPERATING AN EXHAUST-GAS SAMPLING SYSTEM OF SAID TYPE

(71) Applicant: AVL EMISSION TEST SYSTEMS GMBH, Neuss (DE)

(72) Inventors: Sascha Willich, Kaarst (DE); Norbert Kreft, Meerbusch (DE); Christopher Garthe, Kaarst (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 163 days.

(21) Appl. No.: 15/543,236

(22) PCT Filed: Dec. 11, 2015

(86) PCT No.: PCT/EP2015/079424
§ 371 (c)(1),
(2) Date: Jul. 13, 2017

(87) PCT Pub. No.: WO2016/113048
PCT Pub. Date: Jul. 21, 2016

(65) Prior Publication Data
US 2018/0017470 A1    Jan. 18, 2018

(30) Foreign Application Priority Data
Jan. 15, 2015 (DE) .................. 10 2015 100 567

(51) Int. Cl.
*G01N 1/22* (2006.01)

(52) U.S. Cl.
CPC ......... *G01N 1/2252* (2013.01); *G01N 1/2247* (2013.01)

(58) Field of Classification Search
CPC ......... G01N 1/2252; G01N 2001/2255; G01N 1/2247
See application file for complete search history.

(56) References Cited

U.S. PATENT DOCUMENTS

| 6,282,944 B1 * | 9/2001 | Bornemann | G01N 1/2252 73/114.71 |
| 9,297,726 B2 * | 3/2016 | Silvis | G01N 1/2247 |
| 9,389,152 B2 * | 7/2016 | Kumagai | G01N 1/2252 |

(Continued)

FOREIGN PATENT DOCUMENTS

| DE | 198 57 955 A1 | 6/2000 |
| EP | 1 416 260 A2 | 5/2004 |

(Continued)

*Primary Examiner* — Freddie Kirkland, III
(74) *Attorney, Agent, or Firm* — Norman B. Thot

(57) ABSTRACT

An exhaust-gas sampling system includes a main conveying line, a main throughput pump which conveys a sample gas in the main conveying line, a sample gas bag, a sample gas withdrawal line which fluidically connects the main conveying line to the sample gas bag, a throughflow control element arranged in the sample gas withdrawal line, an analyzer, a sample gas analysis line which connects the analyzer to the sample gas bag, an evacuation line which establishes a fluidic connection between the main throughput pump and the sample gas bag, and a first valve arranged in the evacuation line. The first valve opens and closes the evacuation line.

15 Claims, 1 Drawing Sheet

(56) References Cited

U.S. PATENT DOCUMENTS

| | | | |
|---|---|---|---|
| 9,518,897 B2* | 12/2016 | Williamson | G01M 15/10 |
| 10,151,670 B2* | 12/2018 | Silvis | G01N 1/2252 |
| 10,156,500 B2* | 12/2018 | Asami | G01N 1/2252 |
| 2003/0159496 A1* | 8/2003 | McDonald | G01N 1/2258 |
| | | | 73/23.2 |
| 2008/0148813 A1 | 6/2008 | Miyai et al. | |
| 2010/0000339 A1 | 1/2010 | Silvis et al. | |
| 2011/0252864 A1 | 10/2011 | Guenther et al. | |
| 2015/0153254 A1* | 6/2015 | Silvis | G01M 15/10 |
| | | | 73/864 |
| 2017/0074756 A1* | 3/2017 | Williamson | G01M 15/10 |

FOREIGN PATENT DOCUMENTS

| | | |
|---|---|---|
| JP | H10-104134 A | 4/1998 |
| JP | 2008-157682 A | 7/2008 |
| WO | WO 2013/181145 A1 | 12/2013 |

* cited by examiner

EXHAUST-GAS SAMPLING SYSTEM, AND METHOD FOR OPERATING AN EXHAUST-GAS SAMPLING SYSTEM OF SAID TYPE

CROSS REFERENCE TO PRIOR APPLICATIONS

This application is a U.S. National Phase application under 35 U.S.C. § 371 of International Application No. PCT/EP2015/079424, filed on Dec. 11, 2015 and which claims benefit to German Patent Application No. 10 2015 100 567.0, filed on Jan. 15, 2015. The International Application was published in German on Jul. 21, 2016 as WO 2016/113048 A1 under PCT Article 21(2).

FIELD

The present invention relates to an exhaust-gas sampling system comprising a main conveying line, a main throughput pump adapted for conveyance of a sample gas in the main conveying line, a sample gas bag, a sample gas withdrawal line via which the main conveying line is fluidically connectible to the sample gas bag, a throughflow control element arranged in the sample gas withdrawal line, an analyzer which is connectible to the sample gas bag via a sample gas analysis line, and a method for operating an exhaust-gas sampling system of this type, wherein, for withdrawing sample gas, the exhaust gas source is switched on, the main throughput pump is switched on for conveyance of a sample gas through the main conveying line, the throughflow controller or the switching valve in the sample gas analysis line is closed, and, thereafter, for sample gas analysis, the throughflow controller or the switching valve in the sample gas analysis line is opened, the sample gas conveyor is switched on, and, in the analyzer, the sample gas from the sample gas bag is analyzed.

BACKGROUND

Exhaust-gas sampling systems and the appertaining methods for their operation have previously been described and are subject to legal regulations to the effect that the motors of automobiles are not allowed to exceed specific emission limits, such as, for example, the ECE Guideline R 83 for the territory of Europe or the Code of Federal Regulations No. 40 for the United States. These regulations for the most part govern not only the emission limits, but also the type of sampling by systems with variable dilution for emission measurement.

Systems of the above type are known, for example, as CVS systems (constant volume sampling). In these systems, the exhaust gas is admixed with a quantity of air to generate a largely constant total volume flow of the air/exhaust mixture. The samples removed from such systems in bags are then analyzed for their emission contents with the aid of an analyzer. There will in particular be measured carbon dioxide, carbon monoxide, hydrocarbon, and nitrogen oxide contents.

A residue of the sample gas will normally remain in the sample bags after analysis. Before starting a new drive cycle, it is thus required that the sample bags be completely evacuated. This is usually performed by a vacuum pump which is arranged in a separate evacuation line leading to an outlet.

A device of the above type is described, for example, in DE 198 57 955 A1 where the sample bags are arranged within a pressure-tight container adapted to be evacuated via a vacuum conveying means. In the evacuation line as well as in the main conveying lines which lead to the sample bags, and in the lines leading to the analyzer, respective valves are arranged by which the lines can be closed or cleared. The container is subjected to a constant vacuum during the filling of the bags, thus avoiding condensation of the water vapor existent in the exhaust gas. By opening the outlet valves of the sample bags (after the measurement has been performed), the sample bags will also be completely evacuated by the vacuum conveying means.

For space- and cost-saving reasons, the vacuum conveying means is realized in the form of relatively small pumps with small conveying capacities. This has the consequence that the time for evacuation, and thus the time between two to-be-measured drive cycles, is relatively long.

SUMMARY

An aspect of the present invention is to provide an exhaust-gas sampling system and an appertaining system by which a distinctly faster evacuation is accomplished without requiring increased space, increased investment, and/or increased operating costs due to the use of larger pumps.

In an embodiment, the present invention provides an exhaust-gas sampling system which includes a main conveying line, a main throughput pump configured to convey a sample gas in the main conveying line, a sample gas bag, a sample gas withdrawal line configured to fluidically connect the main conveying line to the sample gas bag, a throughflow control element arranged in the sample gas withdrawal line, an analyzer, a sample gas analysis line configured connect the analyzer to the sample gas bag, an evacuation line configured to establish a fluidic connection between the main throughput pump and the sample gas bag, and a first valve arranged in the evacuation line. The first valve is configured to open and close the evacuation line.

BRIEF DESCRIPTION OF THE DRAWING

The present invention is described in greater detail below on the basis of embodiments and of the drawing in which.

DETAILED DESCRIPTION

Figure 1:
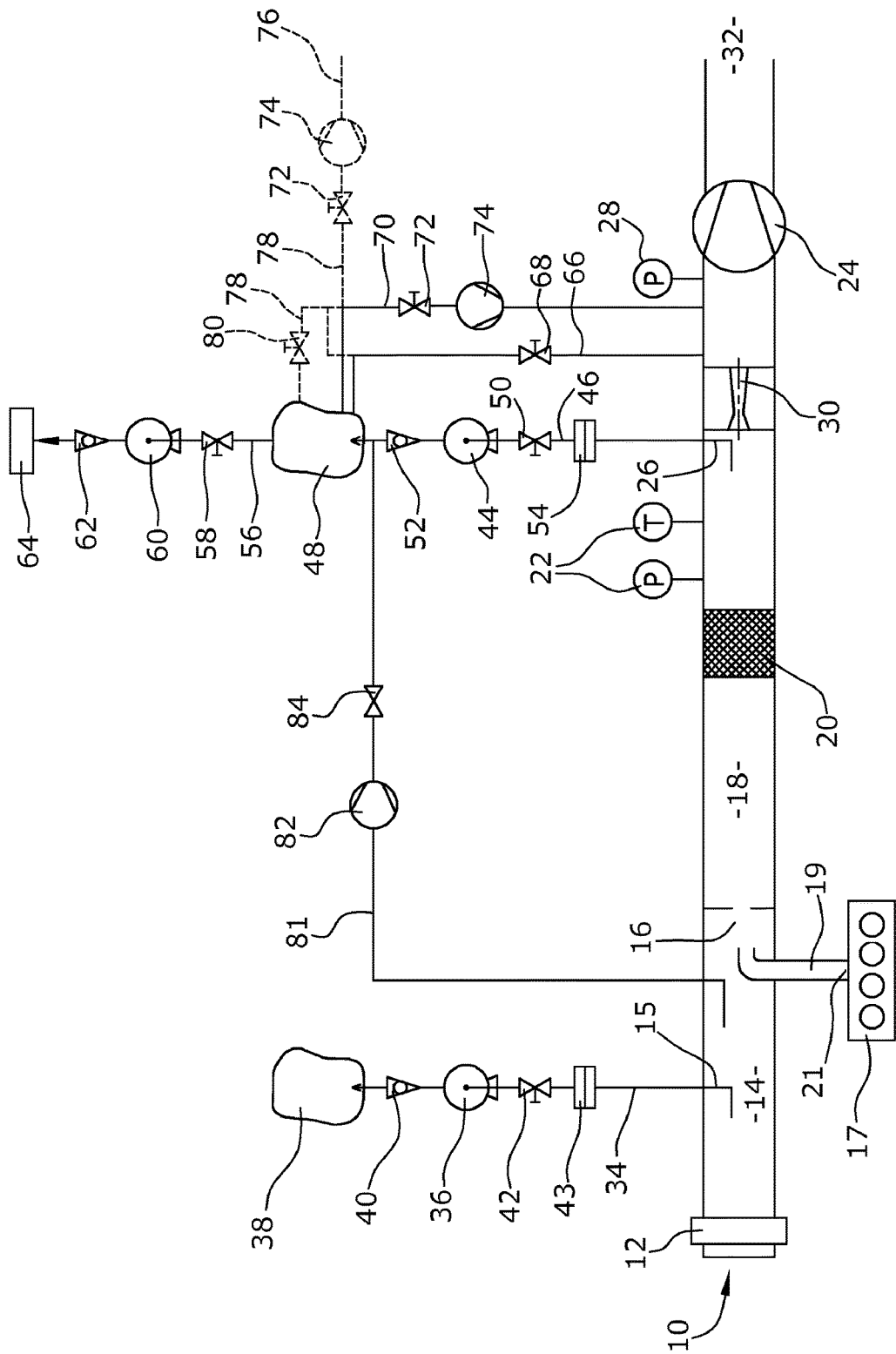
FIG. 1 shows a schematic diagram of an exhaust-gas sampling system according to the present invention in the form of a flow diagram.

Since an evacuation line in the above exhaust-gas sampling system makes it possible to establish a fluidic connection between the main throughput pump and the at least one sample gas bag and a valve is arranged in the evacuation line via which the evacuation line can be closed and opened, it is effected that, during evacuation of the bags, the main throughput pump will be additionally connected. This pump has a distinctly higher throughput than the vacuum pumps normally used for evacuation so that, via the additional connection of this evacuation line, the evacuation time is clearly reduced.

Concerning the method, the exhaust-gas sampling is performed in that, during the withdrawal of sample gas and during the exhaust gas analysis, the valve in the first evacuation line is in a closed state, and, for evacuation of the sample gas bags, the valve in the evacuation line is opened while the main throughput pump is in a switched-on state. A correspondingly fast evacuation of the sample bags will thereby be effected. No additional operating costs are incurred because the main throughput pump is in any event during this time to clear the main conveying line of residual exhaust gases left from the previous drive cycle after the switch-off of the exhaust gas source. The main throughput pump is thus used for evacuation both of the main conveying line and of the sample bags.

The main throughput pump is correspondingly in the switched-on state during the sample gas withdrawal, the sample gas analysis, and the evacuation of the sample gas bags. A renewed start-up of the main throughput pump is thus not necessary.

In an embodiment of the present invention, the evacuation line can, for example, enter into the main conveying line upstream of the main throughput pump. The length of the connection line to the main throughput pump can thus be minimized because a section of the main conveying line is also used for evacuation of the sample bags.

In an embodiment of the present invention, the evacuation line can, for example, enter into the main conveying line downstream of the sample gas withdrawal line. No stress will thus be imposed by the exhaust gas removed from the sample bags on the main conveying line in the section of the main conveying line that is relevant for the measurements. The effectiveness of the rinsing of the main conveying line performed during the second step will thus not be impaired.

In an embodiment of the present invention, the evacuation line can, for example, enter into the main conveying line downstream of a throughflow controller arranged in the main conveying line. In this region between the nozzle and the pump, a vacuum sufficient for evacuation can be generated in the evacuation line with the aid of the main throughput pump.

In an embodiment of the present invention, the throughflow controller can, for example, be realized as a Venturi nozzle which can in particular be operated supercritically so as to allow for proportional sampling.

In an embodiment of the present invention, a vacuum pump can, for example, be arranged in the evacuation line. The vacuum in the evacuation line can thereby be increased and the evacuation time can thus be reduced.

In an embodiment of the present invention, a first evacuation line and a second evacuation line can, for example, be fluidically connectible to the at least one sample gas bag, the second evacuation line having the vacuum pump arranged therein. Parallel to the conveying of the sample gas from the bags by use of the main throughput pump, an additional evacuation is thus performed so that the emptying of the bags will be further accelerated or a still better evacuation with higher obtainable vacuum will be achieved when the first line is closed.

In an embodiment of the present invention, the second evacuation line can, for example, also enter into the main conveying line upstream of the main throughput pump. This reduces the required line lengths, enhances the gas conveyance of the pump, and allows for common discharge of all exhaust-gas-containing samples so that, subsequently, there is no need to use several parallel exhaust gas cleaning means such as, for example, filters or catalysts, if an additional cleaning is provided.

The second evacuation line has a valve arranged therein in order to be able to fully prevent a flow through the second evacuation line during the sampling and during the exhaust gas analysis.

During evacuation of the sample bags, the vacuum pump in the second evacuation line can, for example, be in a switched-on state and the valve in the second evacuation line or the valve in said line section can, for example, be in an open state. During the third step, a maximum flow through the second evacuation line and thus an evacuation of the sample bags with maximum speed is thus safeguarded.

It can alternatively be advantageous if the first evacuation line and the second evacuation line comprise a common line section having the valve arranged therein. Correspondingly, for evacuation of the sample bags, merely one valve instead of two valves in the two evacuation lines needs to be used and respectively switched, with a resultant reduction of production and operating costs. It will, however, only be possible to open and close both lines jointly in such a case.

The sample gas analysis line has a sample gas conveyor and a throughflow controller or a switching valve arranged therein to safeguard a possible conveyance of sample gas from the sample bags to the analyzer and, additionally, a possible shut-off of the sample gas analysis line during the phases when no analyses are performed.

In an embodiment of the present invention, the main conveying line can, for example, comprise an air inlet with a filter, and an exhaust gas inlet which is connected to an exhaust gas source. The sample gas can be made available for sampling in a desired dilution ratio by adjusting the main throughput.

There are thus provided an exhaust-gas sampling system and a method for operating an exhaust-gas sampling system of this type, whereby the cycle times for exhaust gas analysis can be distinctly reduced compared to previously described solutions by reducing the evacuation times of the sample bags and by making it possible to evacuate a plurality of sample bags simultaneously. The production and operating costs can at the same time remain largely unchanged.

An exemplary embodiment of an exhaust-gas sampling system according to the present invention is shown in FIG. 1 as a schematic diagram and, just as the appertaining method for control, will be described below.

The exhaust-gas sampling system of the present invention comprises an air inlet 10 with an air filter 12 arranged thereon. The air will enter into an air duct 14 having an air sampling probe 15 extending into it which, during the measurement process, will continuously take air samples. The air duct 14 enters into a mixing zone 16 where the air is homogeneously mixed with exhaust gas from an exhaust gas source 17 which is connected to an exhaust gas inlet 21 entering into an exhaust gas duct 19. The mixing zone 16 forms the first section of a main conveying line 18 which is flowed through by the sample gas comprising air and exhaust gas. In the main conveying line 18, a device 20 is arranged to condition the sample gas, such as, for example, a heat exchanger for setting a fixed temperature of the sample gas. A measuring device 22 for temperature and pressure measurement is arranged immediately before a main throughput pump 24 operative for conveyance of the sample gas through the main conveying line 18.

The main conveying line 18 has one or a plurality of sampling probes 26 extending therein for taking a representative sample of the test gas. The main throughput pump 24 will safeguard a sufficient throughput in the main conveying line 18. Immediately before the main throughput pump 24, a pressure measuring device 28 is arranged for measuring the pressure before the main throughput pump 24. In this manner, when a throughflow controller 30 in the main conveying line 18 is realized in the form of a Venturi nozzle operating in the supercritical range, it is safeguarded that a sufficient pressure is provided for providing a critical operation of the Venturi nozzle arranged before the main throughput pump 24, wherein, according to the laws of fluid mechanics, the throughflow of the Venturi nozzle is moving at sound velocity so that the Venturi nozzle will serve as the throughflow controller 30. It should be noted, however, that the systems can also be run in the subcritical range. The outlet 32 of the main conveying line 18 is arranged behind the main throughput pump 24.

The air sampled via the air sampling probe 15 is conveyed via an air sample line 34, with the aid of an air conveying pump 36, into a collection bag 38. To allow for withdrawal of this air flow in a constant manner and in a clean state, the air sample line 34 has arranged in it a throughflow controller 42 connected to a throughflow measuring device 40, and an additional air filter 43.

Via the one or a plurality of sampling probes 26, the sample gas is conveyed, with the aid of a sample gas conveying pump 44, via a sample gas withdrawal line 46, into one or a plurality of test gas bags 48. A throughflow control element 50 is arranged upstream of the sample gas conveying pump 44 in the sample gas withdrawal line 46, the throughflow control element 50 being controlled correspondingly to the measurement values of a throughflow measuring device 52 arranged downstream of the sample gas conveying pump 44 so as to maintain the throughflow quantity during gas sampling at a constant level or a level proportionate to the total throughflow, and to safeguard a sufficient sample size at the end of the drive cycle. The throughflow control element 50 and the throughflow measuring device 52 can be formed by a further Venturi nozzle which will generate a throughflow quantity that is proportionate to the throughflow in the main conveying line 18 because the pressure and temperature at both Venturi nozzles are identical. A filter 54 for separation of solid particles is also arranged in the sample gas withdrawal line 46.

The sample gas bag 48 is further connected to one or a plurality of analyzers 64 via a sample gas analysis line 56 in which a throughflow controller or a switching valve 58 as well as a sample gas conveyor 60 and a further throughflow measuring device 62 are arranged. The pollutants in the exhaust gas are determined via the analyzer 64, in particular the contents of hydrocarbons, carbon dioxide, carbon monoxide, and nitrogen oxides in the exhaust gas.

Since this analysis will not require the complete quantity of sample gas stored in the sample gas bags 48, the bags must be completely emptied after the exhaust gas analysis before the next measurement is performed. The sample gas bags 48 will first usually be emptied and then subsequently be rinsed via a purging gas line 81 and, with the aid of a blower 82, via a purging gas withdrawn downstream of the filter 12 being conveyed into the sample gas bags 48 and then being evacuated. An open-and-close valve 84 is arranged in the purging gas line 81 to open and close the purging gas line 81.

According to the present invention, the exhaust-gas sampling system comprises, for evacuation of the sample gas bags 48, a first evacuation line 66 which, from the sample gas bag 48, enters into the main conveying line 18 upstream of the main throughput pump 24 and downstream of the one or a plurality of sampling probes 26 so that a fluidic connection exists between the sample gas bag 48 and the main throughput pump 24. This fluidic connection can be closed or opened by a valve 68 disposed in the first evacuation line 66.

In addition to the first evacuation line 66, the illustrated exhaust-gas sampling system comprises a further, second evacuation line 70 which again has a valve 72 arranged therein so that the second evacuation line 70 can also be closed or cleared by the valve 72. A vacuum pump 74 is additionally arranged in the second evacuation line 70, the vacuum pump 74 being adapted to apply additional vacuum for evacuating the sample gas bags 48, vacuum pump 74 having a distinctly lower maximum throughput than the main throughput pump 24. FIG. 1 shows, via the solid line, that the second evacuation line 70 also enters into the main conveying line 18 before the main throughput pump 24. This system offers the advantage that the entire exhaust gas is conducted to the outside via one outlet. It can also be provided, however, as indicated by the interrupted lines, that the second evacuation line 70 leads to a separate outlet 76.

It can further be envisioned that both evacuation lines 66, 70 comprise a common line section 78 which only in a further course will divide into the first evacuation line 66 and the second evacuation line 70. In the common line section 78, a valve 80 is arranged for replacement of valve 72 so that either both evacuation lines 66, 70 will be cleared or closed together or, alternatively, both evacuation lines 66, 70 will be closed by valve 80 and, with the second evacuation line 70 in its opened state, the first evacuation line 66 can be closed by valve 68.

When the exhaust-gas sampling system is to be operated, a test cycle will be started by switching on the exhaust gas source 17. At this time, the main throughput pump 24 conveys the sample gas through the main conveying line 18. Via the air sampling probe 15, a sample air flow is conveyed through the air sample line 34 from air duct 14 to the collection bag 38 with the aid of the air conveying pump 36. At the same time, the sample gas comprising exhaust gas and air is conveyed, with the aid of the sample gas conveying pump 44 and via one or a plurality of sampling probes 26, through the sample gas withdrawal line 46 to the one or plurality of test gas bags 48. This sampling, i.e., the withdrawn sample gas flow, is achieved by use of the critical Venturi nozzles 30, 50 in proportion to the total gas flow. The valve 68 in the first evacuation line 66, the valve 72 in the second evacuation line 70, and the throughput controller or the switching valve 58 in the sample gas analysis line 56, are closed at this point in time so that no sample gas can escape from the sample gas bags 48. The vacuum pump 74 and the sample gas conveyor 60 are correspondingly also in a non-operating state.

The sample gas conveying pump 44 will be switched off upon completion of the test cycle. In this second step, the sample gas conveyor 60 will additionally be switched on and the switching valve 58 will be opened, resulting in conveyance of sample gas from the sample gas bags 48 through the sample gas analysis line 56 to the analyzer 64. The main throughput pump 24 continues to be operated for suctional removal of residual gas existent in the main conveying line 18 during this process.

The sample gas bags 48 must be completely evacuated in a third step after all analyses have been carried out. For this purpose, both valves 68, 72 are opened and the vacuum pump 74 is switched on so that, via the two evacuation lines 66, 70, the residual sample gas existent in the sample gas bags 48 will flow back into the main conveying line 18. In the process, the required pressure gradient is generated in the second evacuation line 70 by the vacuum pump 74, and in the first evacuation line 66 by the main throughput pump 24 that is still running. Although the main throughput pump 24 continues to suck air via air filter 12 into the main conveying line 18 at this time, there is also generated a sufficient pressure gradient via the first evacuation line 66, particularly by the Venturi nozzle 50 arranged between the air filter and the main throughput pump 24 and before the inlet of the evacuation lines 66, 70 into the main conveying line 18, in particular because the conveying rate of the main throughput pump 24 is a multiple of that of the vacuum pumps of the type otherwise used. After this evacuation, the sample gas bags 48 are normally once more rinsed via purging gas line 81 and subsequently are evacuated again. It is of course possible to also connect the collection bags 38 to the main conveying line 18 and to evacuate them in the same manner as the sample gas bags 48. For this purpose, there can either be provided separate lines leading directly to the main conveying line 18 and comprising the corresponding valves, or the collection bags 38 can be fluidically connected to one or both of the evacuation lines 66, 70, 78.

Via this system and the appertaining method, it is thus rendered possible to achieve a distinctly reduced evacuation time for emptying the sample gas bags without the need for an additional conveyor. The relevant constructional changes can consequently be made largely without incurring additional costs. It may even be possible to reduce costs, in particular when omitting the additional vacuum pump. Operating costs are lowered irrespective of whether one or two evacuation lines are used since the time for emptying the bags is reduced and the vacuum pump thus needs to run for a shorter time.

It should be clear that various modifications can be envisioned within the protective scope of the claims. Other than in the above described embodiment, it may in particular be possible, depending on the circumstances, to omit a second evacuation line. The two evacuation lines can also be partly combined, thus obviating the need for a control valve. Other than in the above described embodiment, one or a plurality of sample gas bags will normally be filled in parallel or after each other. It is explicitly noted that the exhaust-gas sampling system of the present invention and the appertaining method are not restricted to sampling with only one bag. Such systems are usually equipped with a plurality of sample gas bags and/or a plurality of sample gas probes which then must be provided with a corresponding number of valves and throughflow controllers in a known manner. All sample bags existing in the system that must be evacuated, in particular also the air collection bags, can also be emptied via evacuation lines connected in the above manner. Reference should also be had to the appended claims.

What is claimed is:

1. An exhaust-gas sampling system comprising:
   a main conveying line;
   a main throughput pump configured to convey a sample gas in the main conveying line;
   a sample gas bag;
   a sample gas withdrawal line configured to fluidically connect the main conveying line to the sample gas bag;
   a throughflow control element arranged in the sample gas withdrawal line;
   an analyzer;
   a sample gas analysis line configured connect the analyzer to the sample gas bag;
   an evacuation line configured to establish a fluidic connection between the main throughput pump and the sample gas bag; and
   a first valve arranged in the evacuation line, the first valve being configured to open and close the evacuation line.

2. The exhaust-gas sampling system as recited in claim 1, wherein the evacuation line is further configured to enter into the main conveying line upstream of the main throughput pump.

3. The exhaust-gas sampling system as recited in claim 1, wherein the evacuation line is further configured to enter into the main conveying line downstream of the sample gas withdrawal line.

4. The exhaust-gas sampling system as recited in claim 1, further comprising:
   a throughflow controller arranged in the main conveying line;
   wherein,
   the evacuation line is further configured to enter into the main conveying line downstream of the throughflow controller.

5. The exhaust-gas sampling system as recited in claim 4, wherein the throughflow controller is a Venturi nozzle.

6. The exhaust-gas sampling system as recited in claim 1, further comprising:
   a vacuum pump arranged in the evacuation line.

7. The exhaust-gas sampling system as recited in claim 6, wherein,
   the evacuation line comprises a first evacuation line and a second evacuation line which are each configured to be fluidically connectible to the sample gas bag, and
   the vacuum pump is arranged in the second evacuation line.

8. The exhaust-gas sampling system as recited in claim 7, wherein the second evacuation line is configured to enter into the main conveying line upstream of the main throughput pump.

9. The exhaust-gas sampling system as recited in claim 7, wherein the first evacuation line and the second evacuation line each comprise a common line section in which the first valve is arranged.

10. The exhaust-gas sampling system as recited in claim 9, further comprising:
    a second valve arranged in the second evacuation line.

11. The exhaust-gas sampling system as recited in claim 10, further comprising:
    a sample gas conveyor; and
    a throughflow controller or a switching valve,
    wherein, the sample gas conveyor and the throughflow controller or the switching valve are arranged in the sample gas analysis line.

12. The exhaust-gas sampling system as recited in claim 11, wherein the main conveying line comprises an air inlet and an exhaust gas inlet, the exhaust gas inlet being connected to an exhaust gas source.

13. A method for operating the exhaust-gas sampling system as recited in claim 12,
    wherein,
    the first valve is arranged in the first evacuation line,
    the method comprising:
    withdrawing the sample gas by:
       closing the first valve in the first evacuation line,
       switching on an exhaust gas source,
       switching on the main throughput pump to convey the sample gas through the main conveying line, and
       closing the throughflow controller or the switching valve in the sample gas analysis line; thereafter,
    performing a sample gas analysis by:
       opening the throughflow controller or the switching valve in the sample gas analysis line,
       switching on the sample gas conveyor, and
       analyzing the sample gas from the sample gas bag in the analyzer; and
    thereafter
    evacuating the sample gas bag by:

opening the first valve in the first evacuation line, and maintaining the main throughput pump in a switched-on state.

14. The method according to claim 13, wherein, during each of the withdrawing of the sample gas, the performing of the sample gas analysis, and the evacuating of the sample gas bag, the method further comprises:
   maintaining the main throughput pump in the switched-on state.

15. The method according to claim 13, wherein,
   the first valve is arranged in the common line section, and
   during the evacuating of the sample gas bag, the method further comprises:
   switching on the vacuum pump in the second evacuation line, and
   opening and the second valve in the second evacuation line or opening the first valve in the common line section.

* * * * *